United States Patent [19]

Graf von Berckheim

[11] 4,025,323

[45] May 24, 1977

[54] ELECTROSTATIC PRECIPITATOR WITH TELEVISION RECEIVER

[76] Inventor: Constantin Graf von Berckheim, Friedrichstrasse 9, Weinheim, Germany

[22] Filed: Feb. 4, 1976

[21] Appl. No.: 655,043

[30] Foreign Application Priority Data

Feb. 22, 1975 Germany .................. 2507794

[52] U.S. Cl. .................. 55/139; 55/148; 55/150; 313/51; 358/245; 361/230
[51] Int. Cl.² .................. B03C 3/00
[58] Field of Search .......... 55/105, 139, 148, 150, 55/151; 317/3, 4, 262 AE; 178/7.8, 7.5 R, DIG. 11; 315/411; 339/154 A; 313/51

[56] References Cited

UNITED STATES PATENTS

| 3,469,031 | 9/1969 | Selchell | 55/139 |
| 3,680,281 | 8/1972 | Jahnke et al. | 55/150 |

FOREIGN PATENTS OR APPLICATIONS

| 897,095 | 11/1953 | Germany | 55/139 |

*Primary Examiner*—Bernard Nozick

*Attorney, Agent, or Firm*—Burgess, Dinklage & Sprung

[57] ABSTRACT

A connector set is provided for use in apparatus for the production of a direct-current electrostatic field, comprising a first electrode situated, e.g., near a room ceiling, connected to the high direct-current voltage power supply of a television receiver, and a counterelectrode at ground potential, e.g., the floor and walls of the room; the connector set comprising a very high resistance voltage divider connected between the ground and the high voltage direct-current power supply of the television receiver, a tap in the voltage divider providing a connection to the first electrode and a connector which permits connection of the connector set to the said high direct-current power supply wherein the connector has on one side a first plug-in contact for attachment to the anode plug-in connecting means of the picture tube of the television receiver and a sealing cup surrounding such first plug-in contact, and on the other side a second plug-in contact equal to the anode plug-in connecting means and a surface surrounding the second plug-in contact for engagement with the sealing cup of an anode plug-in contact connected to the high voltage power supply.

19 Claims, 6 Drawing Figures

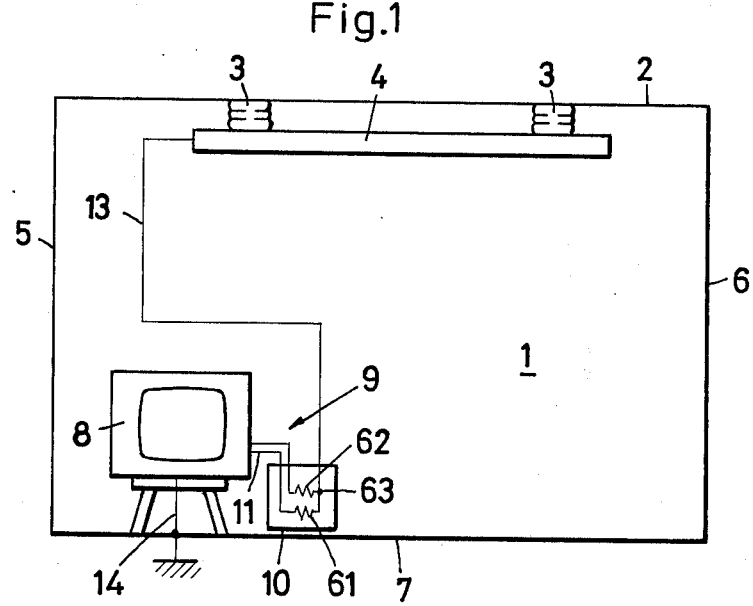
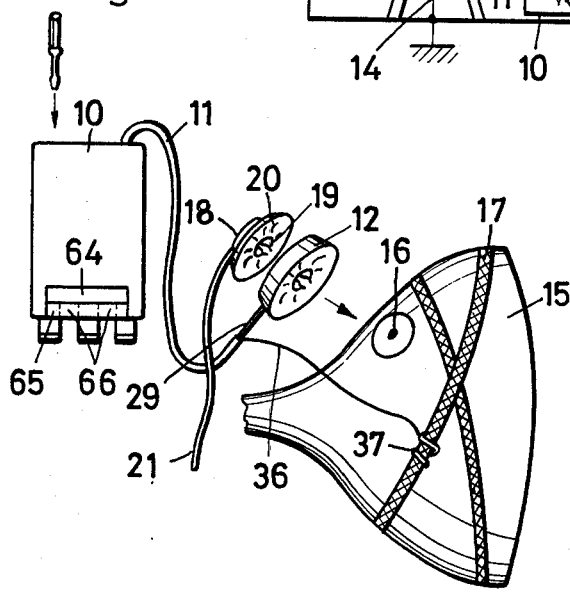
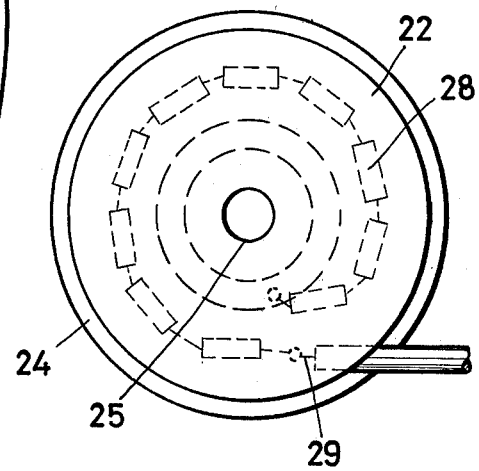
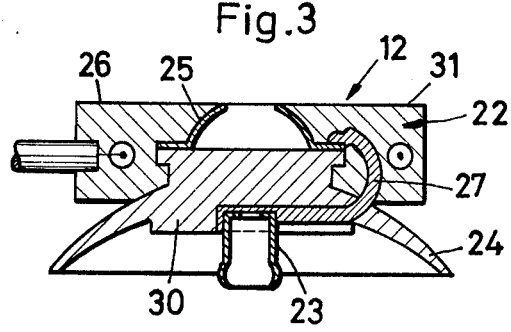

ELECTROSTATIC PRECIPITATOR WITH TELEVISION RECEIVER

BACKGROUND

The invention relates to a connector set for an apparatus for the production of a direct-current electrostatic field, especially for electrostatic air treating installations, having a first electrode connected to a high direct-current voltage and a counterelectrode at ground potential, in which connector set a voltage divider of very high resistance, amounting to at least $10^7$ ohms, and preferably more than $2 \times 10^9$ ohms, is connected between the ground and the picture tube high voltage direct-current power supply of a television receiver, a tap in the voltage divider serving for connection to the first electrode, and a connector being provided which permits connection to the direct-current output.

In a known device of this kind, the direct-current high-voltage output of the television receiver is connected by a conductor to a receptacle into which the connecting plug can be inserted. The other end of the voltage divider is directly connected to ground. A resistance connected to the direct-current high-voltage output is disposed within the connecting plug.

THE INVENTION

The object of the invention is to simplify the installation of the connector set and to improve its safety.

This object is achieved in accordance with the invention by the fact that, in a television receiver having a plug-in-type junction consisting of a socket and plug between the high-voltage power supply and the anode of the picture tube, the connector has on its one side a first plug contact for attachment to the anode terminal of the picture tube and a sealing cup surrounding it, and on its other side a second socket terminal similar to the anode socket terminal surrounded by a surface for sealing engagement with the sealing cup of an anode plug connected to the high-voltage power supply.

In this design, the anode terminal connecting means already available is utilized for the derivation of the high-voltage potential. To install the connector set it is necessary only to remove the anode plug from the picture tube anode socket and insert the connector between the anode socket and the anode plug. This can be accomplished without difficulty after removing the back of the television receiver, and it takes but little time.

If a resistor of the voltage divider is disposed within the connector in a known manner, greater safety is provided in comparison to a high-voltage receptacle mounted on the outside wall of the television receiver, because the current flowing in the parts outside of the receiver will then be limited to a very low level by this resistor.

It is especially advantageous for the ground connection of the voltage divider to be provided with a terminal for connection to the mass potential of the television receiver. Preferably the terminal is adapted for attachment to the shielding of the picture tube, so that the ground connection will be close to the high-voltage connection to facilitate retrofitting. The connection, however, can also be made to the chassis, for example. The terminal is therefore on the interior of the television receiver as is also the connector, and it can be conveniently installed after removing the back of the receiver. Even when the mass potential differs from the ground potential, and consequently the voltage divider is connected to ground indirectly through the mass potential, definite advantages result, because the mass potential is a direct current voltage which is incorporated additively into the derived voltage.

It is especially desirable for the connector to be connected to at least a portion of the voltage divider by one conductor of a two-conductor cable whose other conductor serves for connecting the ground terminal of the voltage divider to the mass potential of the television receiver. In this case the second conductor can especially form the shielding of the first conductor. If the voltage divider or a portion thereof is located outside of the television receiver, a two-conductor cable will suffice to provide the high-voltage connection and the ground connection in the television receiver.

If a resistor of the voltage divider is located within the connector and connected to the high voltage direct-current output, it is desirable that it be located in the body of the connector away from the central axis of the plug. In this manner the space available beneath the surface adapted for sealing engagement with the anode plug sealing cup can be utilized. In particular, the connector can then be made flat.

To special advantage the resistor is divided into a plurality of individual resistors connected in series. Each individual resistor will then carry only a fraction of the total voltage. It will then be possible to use inexpensive resistors or correspondingly lower ability to withstand high voltages.

Moreover, the individual resistors can be disposed in a circle in the body of the connector. In this manner, especially good use can be made of the space available beneath the sealing cup engaging surface. Also, if the resistors are arrayed in zig-zag formation sufficient spacing between the remote ends of adjacent resistors can be obtained for the high-voltage insulation.

In a preferred embodiment, a housing separate from the connector is provided, in which at least two voltage dividier resistances are provided with a fixed tap between them.

Another possibility consists in providing a housing separated from the connector, in which at least one potentiometer resistance, an adjustable tap, a displacing mechanism for that purpose, and a high-voltage plug socket affixed to the housing are provided. This housing, which can be disposed outside of the television receiver, then makes possible the connection of the first electrode as well as the adjustment of the desired voltage.

Also, a plurality of potentiometer resistances can be connected electrically in series and be disposed adjacent one another in the housing, an adjustable tap, a displacing mechanism and a high-voltage plug socket being able to be associated with each of these resistances. In this manner the possibility is provided for deriving and adjusting a plurality of voltages within a minimum of space.

Preferably, holes are provided in the housing wall in the axial prolongation of adjusting spindles, and each adjusting spindle is provided with an insulated head facing the hole and containing a slot for engagement by a screwdriver. In this manner an adjustment of the tap voltage can be undertaken even while the receiver is on. Still other insulating members can, of course, be interposed in addition to the insulating head; for example, the adjustable cap can be held by the adjusting spindle by means of an insulating body. Also, an insulated screwdriver can be used.

Furthermore, the housing and its cover can consist of plastic, and can have shielding connected to the ground connection of the voltage divider for the prevention of the build-up of a charge on the interior.

In another embodiment, provision is made for all of the resistances of the voltage divider to be disposed in the body of the connector, and the tap on the voltage divider is permanently set within the body. By this design a very simple connector set is achieved, because all the important parts are housed in the connector. Also, no adjusting means is necessary.

If adaptation of the derived voltage to various operating conditions is desired, at least one of the resistors can be installed interchangeably. The desired derived voltage will then be obtained by means of the insertion of resistors of appropriate size.

Advantageously, provision is made for potting the fixedly installed resistances, taps and high-voltage sockets in the body of connector with an insulating material. In this manner the ability to withstand high voltages is improved.

It is furthermore desirable for the housing to be provided with means for fastening to the back of the television receiver. All of the components required for the production of the desired high voltage are then directly combined with the television receiver. The set can in this case be a series-manufactured unit. If desired, it can suffice to replace the back with another matched to the cabinet.

The invention will now be further explained with the aid of the embodiments represented in the drawing, wherein:

FIG. 1 is a diagrammatic representation of a room with an electrostatic air treatment installation, which is supplied by a connector set in accordance with the invention;

FIG. 2 is a perspective representation of the important parts of a connector set in accordance with the invention;

FIG. 3 is a longitudinal cross sectional view taken through a connector of FIG. 2, FIG. 4 is a rear elevational view of the connector of FIG. 3.

Figure 5:
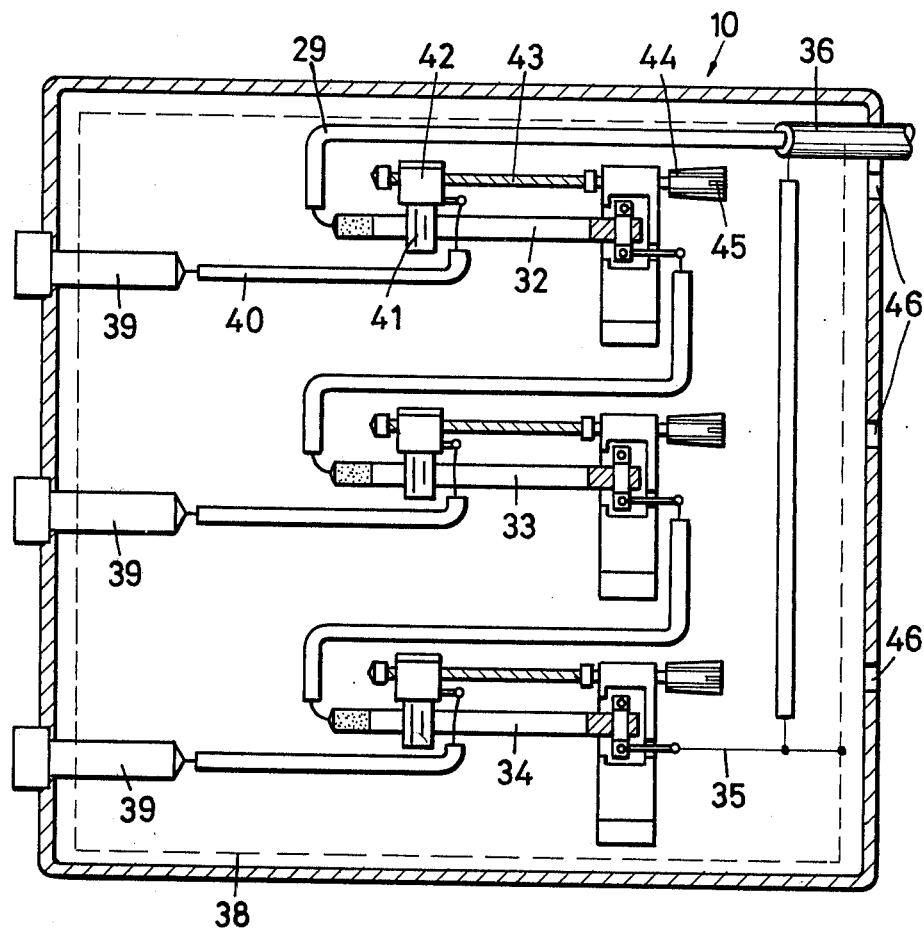
FIG. 5 is a cross sectional view taken through a tap housing of FIG. 2.

In a room 1 a ceiling electrode 4 is mounted on the ceiling 2 by means of insulators 3. The side walls 5 and 6 and the floor 7 of the room are at ground potential and form a counterelectrode to the ceiling electrode 4. In the room there is a television receiver 8 with a connector set 9 of which here only a tap housing 10 and a two-conductor cable 11 can be seen, while a connector 12 (FIG. 2) is located in the interior of the television receiver 8. A conductor 13 supplying high voltage to the ceiling electrode 4 leads directly from the tap housing 10 to this electrode. The television receiver 8 is in turn grounded through a conductor 14.

In FIG. 2 is represented the picture tube 15 of the television receiver, whose anode is adapted in a conventional manner for connection to the high-voltage supply by means of a connector having two plug-in type contacts. The picture tube is provided with an anode plug socket 16 and a shield 17 which is at mass potential. An anode plug 18 has a plug pin 19 and a sealing cup 20 surrounding the latter. The plug pin 19 is connected by a conductor 21 to the high-voltage power supply of the television receiver. Ordinarily the plug pin 19 is engaged directly in the socket 16 on the picture tube. The reverse arrangement is also possible, in which the picture tube bears the pin and the anode connector bears the socket. In the present case, the connector 12 is interposed between the anode plug 18 and the plug socket 16.

As seen in FIGS. 3 and 4, the connector 12 is provided with a body 22 which has on the one side a plug pin 23 for introduction into the anode socket 16 and a sealing cup 24 surrounding the pin, and on the other side a plug socket 25 of a construction similar to the anode socket 16, located in the center of a surface 26 serving for engagement with the sealing cup 20 of the anode plug 18. The plug pin 23 and the plug socket 25 are connected to one another by a conductor 27. In the body 22 beneath the surface 26 a plurality of series-connected resistors 28 are disposed in a circle, said resistors being selected such that the current of the high-voltage power supply will not exceed a prescribed value in the most unfavorable case. The first resistor is connected to the plug socket 25, and the last resistor is connected with one conductor 29 of the cable 11. To simplify manufacture, the body 22 consists of two parts, namely an inner part 30 of more resilient material bearing the plug pin 23 and plug socket 25 and forming the cup 24, and an outer part 31 consisting of cast resin and enveloping the individual resistors 28.

The tap housing 10 of FIG. 5 has three potentiometer resistances 32, 33 and 34 adjacent one another, which are connected electrically in series between the conductor 29 and a ground connection 35. The latter is connected to a shield 36 and to a second conductor 36 which serves as a shield of the first conductor 29. This shielding conductor has at its other end a clip 37 by which it can be attached to a part of the television receiver that is at the mass potential--e.g., the shielding 17 of the picture tube.

The housing 10 consists of plastic and is provided on its interior with a metal shielding 38 which is also connected to the ground terminal 35. The same is the case with the cover, which is not shown, of the housing 10. Also, three sockets 39 are provided in the housing, each of them connected by a conductor 40 to a tap 41. The tap is held by means of an insulating piece 42 on an adjusting spindle 43 which has an insulating head provided with a slot 45. In the axial prolongation of this head there is provided a hole in the housing wall, through which the adjusting spindle can be adjusted by means of an insulated screwdriver, so that the tap 41 will be moved along the potentiometer resistance 32. At least the sockets 39, but also the conductors connected to them, can be potted in an insulating material, such as a synthetic resin.

To connect the connector set 9 to the television receiver it is necessary only to remove the back from the latter, place the connector 12 between the anode plug 18 and the anode socket 16, attach the clip 37 to the shield 17 or to some other conductor leading to a ground potential, and then reinstall the back. This is a very simple, quick operation. Then a plug on the conductor 13 can be inserted into one of the sockets 39 depending on the voltage desired. In one embodiment, voltages between 11 and 16 kV can be derived from the potentiometer resistance 32, voltages between 6 and 11 kV from the potentiometer resistance 33, and voltages between 1 and 6 kV from potentiometer resistance 34. By means of a screwdriver inserted through a hole 46, the desired voltage can be adjusted and, if necessary, readjusted.

Figure 6:
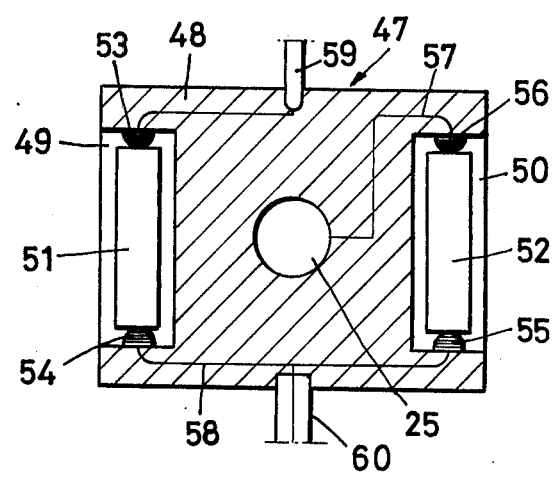
FIG. 6 is a cross sectional view taken through a connector in accordance with another embodiment.

In the embodiment represented in FIG. 6 a connector 47 is of exactly the same construction as connector 12 at its two opposite ends. Consequently it has a plug socket 25. In the body 48 of connector 47, recesses 49 and 50 are provided on the two narrow sides for the accommodation of the resistances 51 and 52, respectively. The extremities of the recesses are provided with the contacts 53, 54, 55 and 56. A conductor 57 connects the plug socket 25 to contact 56. Another conductor 58 connects together the contacts 54 and 55. A third conductor 59 connects contact 53 to a clip corresponding to clip 37 for connection to a conductor in the television receiver which leads to a mass potential. A tap 60 is fixedly connected to conductor 58; it constitutes conductor 13 or is connected thereto by a plug.

In this embodiment, the entire connector set is constituted by the connector 47. If a different voltage is desired at the tap 60, all that is needed is to replace the resistors 51 and 52, either by replacing one with the other, or by replacing them with one or more different resistors.

As it is indicated in FIG. 1, two fixed resistances 61 and 62 can be provided in the connection housing 10, with a fixed tap 63 between them, to which the conductor 13 is connected. These fixed resistances 61 and 62 can also be replaceable. If the desired voltage is unvariable, the resistances can also be completely potted in an insulating plastic. Of course, more than two voltage dividing resistances and more than one tap can be present.

In FIG. 2 there is also shown an L-shaped bracket in whose upstanding limb 65 holes 66 are provided for the accommodation of mounting screws. By means of this bracket 64 the housing 10 can be mounted on the inside of the back cover of the television receiver such that the high-voltage plug sockets can be reached from without. If desired, the back cover can also be molded in a shape which will accommodate the housing 10. Other methods of mounting can also be used, including the mounting of the housing on the outside of the back cover.

What is claimed is:

1. An apparatus for the production of an electrostatic direct-current field having a first electrode to which a high direct-current voltage is applied using the high voltage power supply of a television receiver, and a counterelectrode that is at ground potential, a connector set comprising a voltage divider having a resistance value of at least $10^7$ ohms, connected between the ground and the direct-current output of the high voltage picture tube power supply of the television receiver, a tap on the voltage divider serving as the connection to the first electrode, and a connector providing the connection to the direct-current output of the television receiver, said connector fitting between connecting means consisting of a plug and socket between the high-voltage power supply and the anode of the picture tube of said television receiver, the said connector having on one side a first plug-in contact attached to the anode plug-in connecting means of the picture tube, and a sealing cup surrounding said first plug-in contact, and on the other side a second plug-in contact equal to the anode plug-in connecting means and a surface surrounding the said second plug-in contact in engagement with the sealing cup of an anode plug-in contact connected to the high voltage power supply.

2. Apparatus as claimed in claim 1 wherein the voltage divider has a resistance value of more than $2 \times 10^9$ ohms.

3. Apparatus as claimed in claim 1 wherein a housing separate from the connector is provided, in which at least two voltage divider resistances are provided with a fixed tap disposed between them.

4. Apparatus as claimed in claim 3 wherein at least one resistance is interchangeable.

5. Apparatus as claimed in claim 1 wherein a housing separate from the connector is provided, in which at least one potentiometer resistance, an adjustable tap for same, an adjusting device therefor, and a high-voltage plug socket affixed to the housing are provided.

6. Apparatus as claimed in claim 5 wherein a plurality of potentiometer resistances are connected electrically in series and are disposed adjacent one another in the housing, and with each of these resistances an adjustable tap, an adjusting device and a high-voltage plug socket are associated.

7. Apparatus as claimed in claim 5 wherein are provided in the housing wall in the axial prolongation of adjusting spindles and each adjusting spindle is provided with an insulating head facing the hole and having a slot-like recess for engagement by a screwdriver.

8. Apparatus as claimed in claim 5 wherein the housing with its cover consists of plastic and has on the inside a shield connected to the ground terminal of the voltage divider.

9. Apparatus as claimed in claim 8 wherein the housing is provided with means for fastening to the back cover of the television receiver.

10. Apparatus as claimed in claim 1 wherein fixedly installed resistances, taps, and high-voltage plug sockets are potted in the housing or body of the connector with insulating material.

11. Apparatus as claimed in claim 1 wherein all the resistances of the voltage divider are disposed in the body of the connector and the tap of the voltage divider is fixed within the body.

12. Apparatus as claimed in claim 1 wherein the ground terminal of the voltage divider is provided with a clip for connection to the ground potential of the television receiver.

13. Apparatus as claimed in claim 12 wherein the clip can be attached to the shield of the picture tube.

14. Apparatus as claimed in claim 1 wherein the connector is connected with at least one part of the voltage divider through one conductor of a two-conductor cable whose other conductor serves for the connection of the ground terminal of the voltage divider to the mass potential of the television receiver.

15. Apparatus as claimed in claim 14 wherein the second conductor forms the shielding of the first conductor.

16. Apparatus in whose connector a resistance of the voltage divider is disposed which is connected to the direct current output, as claimed in claim 1, wherein the resistance is disposed within a body bearing the first and second plug-in contact of the connector outside of the center axis of the plug pin.

17. Apparatus as claimed in claim 16 wherein the resistance is divided into a plurality of individual resistors connected in series.

18. Apparatus as claimed in claim 16 wherein the individual resistors are disposed in a circle within the body of the connector.

19. Apparatus as claimed in claim 16 wherein the individual resistors are arranged in a zig-zag configuration within the body of the connector.

* * * * *